United States Patent [19]

Sprague

[11] Patent Number: 6,140,127
[45] Date of Patent: Oct. 31, 2000

[54] METHOD OF COATING AN INTRAVASCULAR STENT WITH AN ENDOTHELIAL CELL ADHESIVE FIVE AMINO ACID PEPTIDE

[75] Inventor: Eugene A. Sprague, San Antonio, Tex.

[73] Assignee: Cordis Corporation, Miami Lakes, Fla.

[21] Appl. No.: 09/025,682

[22] Filed: Feb. 18, 1998

[51] Int. Cl.⁷ .............................. C12N 5/00; C12N 11/08; A61F 2/00; A61K 38/08; C07K 17/08

[52] U.S. Cl. .................... 435/395; 424/423; 424/93.7; 435/180; 435/396; 435/402; 530/330; 530/402; 530/815

[58] Field of Search ................................. 435/180, 395, 435/396, 402; 424/422, 423, 93.7; 530/330, 402, 815

[56] References Cited

U.S. PATENT DOCUMENTS

| | | | |
|---|---|---|---|
| 4,733,665 | 3/1988 | Palmaz | 606/108 |
| 4,739,762 | 4/1988 | Palmaz | 128/343 |
| 4,776,337 | 10/1988 | Palmaz | 128/343 |
| 5,102,417 | 4/1992 | Palmaz | 606/195 |
| 5,116,318 | 5/1992 | Hillstead | 604/96 |
| 5,195,984 | 3/1993 | Schatz | 606/195 |
| 5,278,063 | 1/1994 | Hubbell et al. | 435/240.243 |
| 5,330,911 | 7/1994 | Hubbell et al. | 435/240.243 |
| 5,366,472 | 11/1994 | Hillstead | 606/194 |
| 5,476,476 | 12/1995 | Hillstead | 606/194 |
| 5,643,312 | 7/1997 | Fischell et al. | 606/198 |
| 5,728,751 | 3/1998 | Patnaik | 523/112 |

OTHER PUBLICATIONS

D. M. Brunette, The Effects of Implant Surface Topography on the Behavior of Cells; Int. J. Oral Maxillofac Implants, 1988, pp. 231–246, vol. 3.

Campbell Rogers, Elazer R. Edelman, Endovascular Stent Design Dictates Experimental Restenosis And Thrombosis; Circulation, Jun. 15, 1995, pp. 2995–3001, vol. 91, No. 2, American Heart Association, Inc.

*Primary Examiner*—David M. Naff

[57] ABSTRACT

Endothelial cell attachment to an intravascular stent is promoted by coating the stent with an endothelial cell specific adhesion peptide. Coating is preferably carried out by activating the intravascular stent using plasma glow discharge, applying on the stent a layer or plurality of layers of a polymer such as poly(2-hydroxyethylmethacrylate), applying a tresylation solution containing pyridine and tresyl chloride, and applying a five amino acid peptide having the sequence glycine-arginine-glutamic acid-aspartic acid-valine.

5 Claims, 1 Drawing Sheet

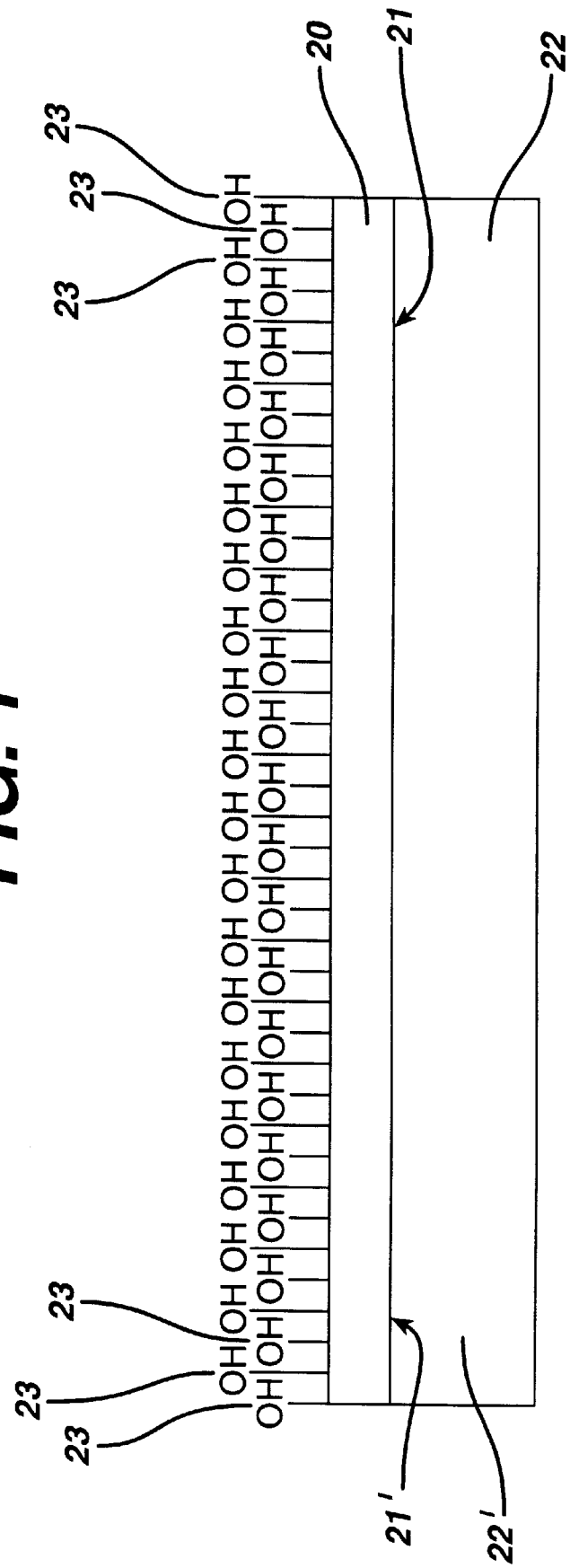

METHOD OF COATING AN INTRAVASCULAR STENT WITH AN ENDOTHELIAL CELL ADHESIVE FIVE AMINO ACID PEPTIDE

BACKGROUND OF THE INVENTION

1. Field of the Invention

The invention relates to an endothelial cell specific adhesion peptide coating which promotes attachment of endothelial cells to prosthetic surfaces. More particularly, the invention relates to an endothelial cell specific adhesion peptide coating which promotes attachment of endothelial cells to an intravascular stent surface, a method of coating an intravascular stent, and a method of promoting endothelial cell attachment to a surface of an object, such as an intravascular stent.

2. Description of Related Art

Although, intravascular stent placement has been demonstrated to be highly efficacious in initially restoring patency to sites of vascular occlusion, intravascular stent placement sometimes shares the common problem of restenosis with other revascularization procedures including bypass surgery and balloon angioplasty. An important factor contributing to this possible reocclusion at the site of intravascular stent placement is injury to, and loss of, the natural nonthrombogenic lining of the arterial lumen, the endothelium. Loss of the endothelium, exposing the thrombogenic arterial wall matrix proteins, along with the generally thrombogenic nature of prosthetic materials, initiates platelet deposition and activation of the coagulation cascade. Loss of the endothelium also at the interventional site may be important to the development and extent of eventual intimal hyperplasia at the site of implantation of the intravascular stent. Rapid re-endothelialization of the arterial wall, as well as endothelialization of the intravascular stent surface are, therefore, important for the prevention of low flow thrombosis, prevention of excessive arterial smooth muscle cell growth, and for continued patency. Re-endothelialization of the arterial wall and endothelialization of the prosthetic surface are achieved primarily by migration of endothelial cells from adjacent arterial areas of intact endothelium to the intravascular stent surface and the arterial walls. Accordingly, it is an object of the invention to increase the rate of migration and attachment of the endothelial cells to the surface of the intravascular stent and the arterial walls.

Prior attempts to prevent restenosis at the site of intravascular stent placement include treating the intravascular surface with anticoagulants and/or smooth muscle cell growth inhibitors. These prior attempts have deficiencies. For example, all of these treatments fail to promote endothelial cell attachment to the intravascular stent surface, and therefore, the rate of endothelialization of the intravascular stent surface is not increased.

Accordingly, prior to the development of the present invention, there has been no composition which promotes the attachment of endothelial cells to the surface of intravascular stents, method of coating intravascular stents, or method of promoting endothelial cell attachment to a surface of an object, which: promotes endothelialization of the intravascular stent or object surface; assists in the prevention of low flow thrombosis; does not interfere with the growth of other intravascular cells; assists in the restoration of patency to the site of vascular occlusion; and assists in prevention of restenosis at the cite of intravascular stent placement. Therefore, the art has sought a composition which promotes the attachment of endothelial cells to the surface of the intravascular stents, a method of coating intravascular stents, and a method of promoting endothelial cell attachment to a surface of an object, which: promotes endothelialization of the intravascular stent or object surface; assists in the prevention of low flow thrombosis; does not interfere with the growth of other intravascular cells; assists in the restoration of patency to the site of vascular occlusion; and assists in prevention of restenosis at the site of intravascular stent placement. It is believed that the present invention will achieve these objectives and overcome the disadvantages of other compositions and methods in the field of the invention, but its results or effects are still dependent upon the skill and training of the surgeon.

SUMMARY OF INVENTION

In accordance with the invention the foregoing advantages have been achieved through the present method of coating an intravascular stent comprising the steps of providing an intravascular stent; and applying an adhesion peptide coating to the intravascular stent, wherein the adhesion peptide coating is a five amino acid peptide. A further feature of the method is that the five amino acid peptide has the sequence glycine-arginine-glutamic acid-aspartic acid-valine.

In accordance with another aspect of the invention, the foregoing advantages have also been achieved through the present method of coating an intravascular stent. This method may include the steps of providing an intravascular stent; activating the intravascular stent; and applying an adhesion peptide coating to the intravascular stent, wherein the adhesion peptide coating is a five amino acid peptide. A further feature of the method is that the intravascular stent is activated by using plasma glow discharge. An additional feature of the method is that the five amino acid peptide has the sequences glycine-arginine-glutamic acid-aspartic acid-valine.

In accordance with another aspect of the invention, the foregoing advantages have also been achieved through the present method of coating an intravascular stent. This method may include the steps of providing an intravascular stent; activating the intravascular stent; applying a polymer to the intravascular stent to form a polymer layer on the intravascular stent; and applying an adhesion peptide coating to the intravascular stent, wherein the adhesion peptide coating is a five amino acid peptide. A further feature of the method is that the intravascular stent includes a plurality of polymer layers. An additional feature of the method is that the intravascular stent is activated by using plasma glow discharge. Another feature of the method is that the five amino acid peptide has the sequence of glycine-arginine-glutamic acid-aspartic acid-valine. A further feature of the method is that the polymer layer is a layer of acrylic resin. An additional feature of the invention is that the acrylic resin is poly(2-hydroxyethylmethacrylate).

In accordance with another aspect of the invention, the foregoing advantages have also been achieved through the present method of coating an intravascular stent. This aspect of the invention may include the steps of providing an intravascular stent; activating the intravascular stent; applying a polymer to the intravascular stent to form a polymer layer on the intravascular stent; applying a tresylation solution to the intravascular stent, wherein the tresylation solution comprises pyridine and tresyl chloride; and applying an adhesion peptide coating to the intravascular stent, wherein the adhesion peptide coating is a five amino acid peptide. A further feature of the invention is that the polymer layer is an acrylic resin. An additional feature of the invention is that the acrylic resin is poly(2-hydroxyethylmethacrylate). Another feature of the invention is that the tresylation solution is dioxane.

In accordance with another aspect of the present invention, the foregoing advantages have also been achieved through the method of promoting endothelial cell attachment to a surface of an object. This method may include the steps of providing an object having a surface; and applying an adhesion peptide to the surface of the object, wherein the adhesion peptide is a five amino acid peptide having the sequence glycine-arginine-glutamic acid-aspartic acid-valine; and placing the object in an environment including endothelial cells.

In accordance with another aspect of the present invention, the foregoing advantages have also been achieved through an adhesion peptide coating composition. The composition may be a poly(2-hydroxyethylmethacrylate) and a five amino acid peptide. A further feature of the adhesion peptide coating composition is that the five amino acid peptide has the sequence glycine-arginine-glutamic acid-aspartic acid-valine.

In accordance with another aspect of the present invention, the foregoing advantages have been also achieved through an adhesion peptide coating composition for promoting endothelial cell attachment to a surface of an object. The composition may be a five amino acid peptide having the sequence glycine-arginine-glutamic acid-aspartic acid-valine.

The adhesion peptide composition, method of coating an intravascular stent, and method of increasing the endothelialization of intravascular stents, when compared with previously proposed prior adhesion peptide compositions, methods of coating intravascular stents, and methods of promoting endothelial cell attachment to a surface of an object have the advantages of: promoting endothelialization of the intravascular stent or object surface; assisting in the prevention of low flow thrombosis; not interfering with the growth of other intravascular cells; assisting in the restoration of patency to the site of vascular occlusion; and assisting in prevention of restenosis at the site of intravascular stent placement.

BRIEF DESCRIPTION OF DRAWINGS

FIG. 1 is an object, such as an intravascular stent, having a polymer layer attached to the surface of the object in accordance with one embodiment of the invention.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defiend by the appended claims.

DETAILED DESCRIPTION AND SPECIFIC EMBODIMENTS

The invention is directed to an endothelial cell specific adhesion peptide coating composition, herein referred to as the adhesion peptide coating, a method of coating an intravascular stent, and a method of promoting endothelial cell attachment to a surface of an object. "Intravascular stent" is herein defined as any prosthesis which may be placed within a body passageway containing endothelial cells such as any vein, artery, or blood vessel within the vascular system. Intravascular stents may be used for such purposes as: (1) supportive intravascular stent placement within blocked arteries opened by transluminal recanalization, or angioplasty, but which are likely to collapse in the absence of an internal support; (2) similar use following catheter passage through mediastinal and other veins occluded by inoperable cancers; and (3) reinforcement of catheter created intrahepatic communications between portal and hepatic veins in patients suffering from portal hypertension. The intravascular stents may be constructed out of stainless steel, titanium or any other material which is suitable of implantation into the body passageway. Preferably, the intravascular stents are constructed out of stainless steel. It is to be understood that any intravascular prostheses or devices which are implanted into the intravascular lumen of animals may be coated with the adhesion peptide coating of the invention. Examples of such intravascular stents include, but are not limited to, those of U.S. Pat. Nos. 4,733,665 and 5,102,417.

The adhesion peptide coating includes a five amino acid peptide having the sequence glycine-arginine-glutamic acid-aspartic acid-valine (sequence 1). This coating promotes endothelial cell attachment and migration onto the intravascular stent surface. In a preferred embodiment, the adhesion peptide coating includes at least one polymer layer on the surface of the intravascular stent. The polymer layer is preferably a hydrogel which absorbs water and provides a high number of available hydroxyl groups to facilitate the binding of the adhesion peptide coating. The polymer layer also preferably prevents attachment of proteins, and thus prevents attachment of cells such as smooth muscle cells, platelets, white blood cells and red blood cells, to the surface of the intravascular stent. Preferably, the polymer layer is an acrylic resin, such as polymers and co-polymers of acrylic acid, methacrylic acid, esters of these acids, or acrylonitrile; methacrylates; polyvinyl alcohols; and glycophase. More preferably, the polymer layer is 2-hydroxyethlmethacrylate (HEMA) or poly(2-hydroxyethylmethacrylate) (polyHEMA). Poly(2-hydroxyethylmethacrylate) is even more preferred.

In another specific embodiment of the invention, an intravascular stent is coated with an adhesion peptide coating composition. The method for coating intravascular stents involves activating the surface of the intravascular stent. Activation of the intravascular stent surface is achieved by etching the intravascular stent surface and removing at least some of the ions attached thereto. This activation makes the surface of the intravascular stent more hydrophilic, thereby allowing improved interaction of the polar adhesion peptide coating. Activation of the intravascular stent surface may be achieved by any method known to persons skilled in the art, such as by treating the intravascular stent surface with a strong acid or base, or by using plasma glow discharge. Preferably, plasma glow discharge is used to activate the intravascular stent surface by placing the intravascular stent within the vacuum chamber of a plasma glow discharge device such as an EMS-100 Glow Discharge Unit (Electron Microscopy Services, Inc., Ft. Washington, Pa.) for an exposure to at least about 10 to about 50 mAmps cathode positive charge direct current for at least about 1 to about 10 minutes. The intravascular stent is preferably placed within the vacuum chamber of the plasma glow discharge for an exposure to at least about 25 to about 35 mAmps cathode positive charge direct charge for at least about 3 to about 6 minutes. After activation, the intravascular stent is ready to be coated with the adhesion peptide coating.

Immediately after the intravascular stent is activated, a polymer layer is applied to the surface of the intravascular stent. The polymer layer may be formed on the surface of the intravascular stent by applying any suitable polymer by any method known to persons skilled in the part. In a preferred embodiment, the polymer layer is applied to the surface of the intravascular stent in liquid form and allowed to dry leaving polymer layer attached to the intravascular stent surface. For example, in a preferred embodiment, 1% polyHEMA methanol solution is applied to the intravascular stent surface. The intravascular stent is allowed to dry, i.e., the methanol evaporates away from the intravascular stent, leaving behind a polymer layer consisting of polyHEMA. After the polymer layer is formed on the intravascular stent surface, the five amino acid peptide is applied to the polymer layer to form the adhesion peptide coating.

The intravascular stent is then placed in a fixed vertical position within a centrifuge tube followed by centrifugation at a speed, and for a time, sufficient to allow removal of excess polymer resulting in a uniform polymer layer on the intravascular stent surface. Preferably, the intravascular stent is centrifuged at 4,000 rpm for at least about 30 seconds. The polymer layer on the intravascular stent is then allowed to dry. Any method known to persons skilled in the art may be used to facilitate drying, e.g., allowing the intravascular stent to dry naturally, i.e., air dry, at room temperature for a time sufficient for the polymer layer to dry. Preferably, the polymer layer on the intravascular stent is allowed to dry at 50° C. for 30 minutes. A second polymer layer may then be applied to the intravascular stent following the same steps as described above. Preferably, at least two polymer layers are applied to the intravascular stent. More preferably, four polymer layers are applied to the intravascular stent.

Referring now to FIG. 1, the resulting polymer layer 20 is attached a surface 21 of an object 22, such as a surface 21' of an intravascular stent 22' such that the hydroxyl group(s) 23 of the polymer layer 20 are oriented away from the surface 21 of the object 22, thereby making the hydroxyl group(s) 23 available as reaction sites for subsequent attachment of the adhesion peptide sequence (not shown).

In a preferred embodiment, the intravascular stent is immersed in a 1% polyHEMA methanol solution for thirty seconds. The intravascular stent is removed from the polyHEMA methanol solution and centrifuged at 4,000 rpm for about 30 seconds. The polymer layer on the intravascular stent is then allowed to dry at 50° C. for 30 minutes. A second polymer layer is applied to the intravascular stent by immersing the intravascular stent in the polyHEMA methanol solution following the same steps as described above. Preferably, after centrifugation and drying, a third, and even more preferably, a fourth polymer layer is formed on the surface of the intravascular stent following the steps described above.

After the intravascular stent is layered with the desired number of polymer layers, it is then treated with a tresylation solution containing pyridine and tresyl chloride. Preferably, the tresylation solution is a carrier for the pyridine and tresyl chloride which is a solvent for pyridine, a stabilizer for chlorinated solvents, and an enhancer of removal of water from the intravascular stent surface. While it is contemplated that any tresylation solution having these properties may be used, preferably the tresylation solution is selected from the group consisting of acetone and dioxane. More preferably, the tresylation solution is dioxane. Pyridine is preferably present in the tresylation solution at a concentration ranging from at least about 20 to about 250 µl per milliliter of tresylation solution. More preferably, pyridine is present in the tresylation solution at a concentration ranging from at least about 70 to about 150 µl per milliliter of tresylation solution. Tresyl chloride is preferably present in the tresylation solution at a concentration ranging from at least about 20 to about 250 µl per milliliter of tresylation solution. More preferably, tresyl chloride is present in the tresylation solution at a concentration ranging from at least about 70 to about 150 µl per milliliter of tresylation solution. In a specific preferred embodiment, pyridine and tresyl chloride are both present in the tresylation solution at a concentration of 100 µl per milliliter of tresylation solution.

Treatment of the intravascular stent with the tresylation solution prepares the hydroxyl groups of the polymer layer to form an amide linkage with the terminal amino group of the adhesion peptide sequence, resulting in the intravascular stent being coated with an adhesion peptide coating. Treatment of the intravascular stent with the tresylation solution results in the hydroxyl group (—OH) of the polymer layer being replaced with a tresylate group ($SO_2\ CH_2\ CF_3$). The tresylation reaction occurs as follows wherein R is the carbon backbone of the polymer which is attached to the intravascular stent:

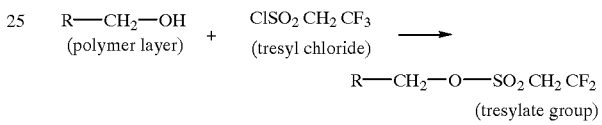

The tresylation solution treatment provides for covalent attachment of the endothelial specific adhesion peptide sequence to the polymer layer, and thus to the surface of the intravascular stent, in a known, specific orientation which increases the number of endothelial cells which can be attached to the intravascular stent. The intravascular stent is treated with the tresylation solution at a temperature, and for an amount of time sufficient, for the tresylation reaction to occur at all, or substantially all, of the hydroxyl groups of the polymer layer. Preferably, the intravascular stents are treated with the tresylation solution at a temperature ranging from at least about 15 to about 40° C. for at least about 5 to about 30 minutes. The intravascular stent is more preferably treated with the tresylation solution at a temperature ranging from at least about 20 to about 30° C. for at least about 10 to about 20 minutes, such that all of the hydroxyl groups of the polymer layer undergo the tresylation reaction.

The intravascular stent is then preferably rinsed with an acid to stabilize the tresylation solution treatment. "Rinsing" is herein defined as washing lightly by letting a solution, such as an acid or a buffer, run over, into, or through the intravascular stent for a short period of time. "Rinsing" also includes dipping the intravascular stent into a solution. The acid preferably has a pH less than about 6. While it is contemplated that any acid having a pH less than about 6 may be used to stabilize the tresylation solution treatment, 1 mM hydrochloric acid is preferred.

Immediately following the rinsing of the intravascular stent with the acid, the intravascular stent is rinsed with a first buffer solution to prepare the intravascular stent for adhesion peptide coupling. Preferably, the first buffer solution has a pH greater than about 8. While it is contemplated that any first buffer solution having a pH greater than about 8 may be used to rinse the intravascular stent, 0.2 M sodium bicarbonate, 0.1 M sodium phosphate, and 0.5 M sodium chloride are preferred. More preferably, the first buffer solution is 0.2 M sodium bicarbonate having a pH of 10.

After the intravascular stent has been rinsed with the first buffer solution, it is treated with a second buffer solution containing at least about 50 to about 500 nanograms per milliliter of the adhesion peptide sequence. Preferably, the second buffer solution is the same as the first buffer solution used to rinse the intravascular stent as described above. The second buffer solution preferably includes at least about 100 to about 300 nanograms per milliliter of the adhesion peptide sequence. The adhesion peptide sequence is a five amino acid sequence having the sequence glycine-arginine-glutamic acid-aspartic acid-valine. The attachment of the adhesion peptide sequence is achieved through the amino terminus of the glycine amino acid. The adhesion peptide sequence binds to the polymer layer (R—CH$_2$) as follows:

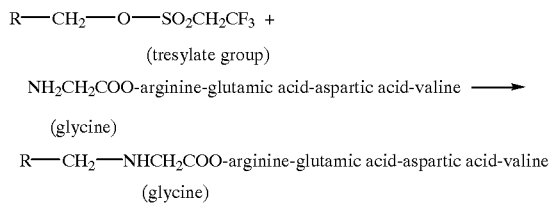

In this arrangement, the glycine acts as a spacer molecule which places the rest of the adhesion peptide sequence in a more accessible position to avoid nonspecific surface interaction with endothelial cell attachment sites on the polymer layer. The intravascular stent being treated with the second buffer solution containing the adhesion peptide sequence is allowed to incubate for an amount of time, and at a temperature, sufficient for the adhesion peptide sequence to bind to all, or substantially all, of the polymer layer attachment sites. Preferably, the intravascular stent is treated with the second buffer solution containing the adhesion peptide sequence at a temperature ranging from at least about 15 to about 40° C. for at least about 1 hour to about 72 hours. More preferably, the intravascular stent is treated with the buffer solution containing the adhesion peptide sequence at a temperature ranging from at least about 20 to about 30° C. for at least about 10 to about 30 hours. During the incubation period, the tresylate group is replaced by the terminal amine group of the adhesion peptide sequence to create an amide linkage between the polymer layer and the adhesion peptide sequence.

After the incubation period, the intravascular stent is rinsed with a blocking solution which prevents non-specific binding of cells to the tresylate groups not bound to the adhesion peptide sequence. While it is contemplated that any blocking solution known to persons skilled in the art may be employed, a 0.8 M solution of mercaptoethanol is preferred.

The intravascular stent is then sterilized by low temperature ethylene oxide, or any other method known by persons skilled in the art. After sterilization, the intravascular stent may be placed into any environment containing endothelial cells such as cell and tissue cultures and body passageways such as veins, arteries, and blood vessels.

In still another embodiment of the invention, the foregoing advantages have been achieved through the present method of promoting endothelial cell attachment to the surface of an object. "Object" is herein defined as any solid or semi-solid surface such as petri dishes, collagen gels, cell culture flasks, or any other object which may be desired to be cultured with endothelial cells in a laboratory setting. After the adhesion peptide coating has been applied to the surface of the object, following the same steps as described above for applying an adhesion peptide coating to the surface of an intravascular stent, the object may then be placed in an environment including endothelial cells. The adhesion peptide coating promotes attachment of endothelial cells to the surface of the object, thereby resulting in rapid endothelialization of the surface of the object. It is contemplated that the endothelial cell specific adhesion peptide sequence increases the rate of confluency of endothelial cells along the surface of the object through migration of the endothelial cells from the environment including endothelial cells to the surface of the object.

It is to be understood that the invention is not limited to the exact details of construction, operation, exact materials, or embodiments shown and described, as obvious modifications and equivalents will be apparent to one skilled in the art. For example, any intravascular prosthesis which may be placed in an environment including endothelial cells, wherein it is desired that endothelialization of the prosthetic surface occur, may be coated in accordance with the invention. Further, the prosthetic devices may be constructed out of many different types of materials, including plastics and fabrics such as suture mesh. Accordingly, the invention is therefore to be limited only by the scope of the appended claims.

What is claimed is:

1. A method of coating an intravascular stent comprising the steps of:

providing an intravascular stent;

activiating the intravascular stent;

applying a polymer to the intravascular stent to form a polymer layer on the intravascular stent;

applying a tresylation solution to the intravascular stent, wherein the tresylation solution comprises pyridine and tresyl chloride;

applying an adhesion peptide coating for adhering cells to the intravascular stent, wherein the adhesion peptide coating is a peptide consisting of five amino acid peptide having the sequence glycine-arginine-glutamic acid-aspartic acid-valine; and wherein the intravascular stent is activated by using plasma glow discharge.

2. The method of claim 1, wherein the intravascular stent includes a plurality of polymer layers.

3. The method of claim 1, wherein the polymer layer is a layer of acrylic resin.

4. The method of claim 1, wherein the acrylic resin is poly(2-hydroxyethylmethacrylate).

5. The method of claim 1, wherein the tresylation solution is dioxane.

* * * * *